US010493134B2

(12) United States Patent
Gueta et al.

(10) Patent No.: US 10,493,134 B2
(45) Date of Patent: Dec. 3, 2019

(54) COMPOSITIONS COMPRISING COLLAGEN AND PRP FOR TISSUE REGENERATION

(71) Applicant: CollPlant Ltd., Nes Ziona (IL)

(72) Inventors: Racheli Gueta, Rechovot (IL); Oded Shoseyov, Karme Yosef (IL); Frida Grynspan Gotlieb, Mevasseret Zion (IL); Ofer Levy, Moshav Ramot Meir (IL)

(73) Assignee: CollPlant Ltd., Rehovot (IL)

( * ) Notice: Subject to any disclaimer, the term of this patent is extended or adjusted under 35 U.S.C. 154(b) by 758 days.

(21) Appl. No.: 14/778,646

(22) PCT Filed: Mar. 19, 2014

(86) PCT No.: PCT/IL2014/050302
§ 371 (c)(1),
(2) Date: Sep. 21, 2015

(87) PCT Pub. No.: WO2014/147622
PCT Pub. Date: Sep. 25, 2014

(65) Prior Publication Data

US 2016/0120955 A1 May 5, 2016

Related U.S. Application Data

(60) Provisional application No. 61/803,856, filed on Mar. 21, 2013.

(51) Int. Cl.
*A61K 38/39* (2006.01)
*A61K 35/16* (2015.01)
*A61K 33/14* (2006.01)
*A61K 35/19* (2015.01)

(52) U.S. Cl.
CPC .............. *A61K 38/39* (2013.01); *A61K 33/14* (2013.01); *A61K 35/16* (2013.01); *A61K 35/19* (2013.01)

(58) Field of Classification Search
CPC ...... A61L 27/24; A61L 29/045; A61L 31/044; A61L 15/325; A61K 8/65; A61K 9/0014; A61Q 19/00; A61Q 19/08; A23L 29/284; C07K 14/78
See application file for complete search history.

(56) References Cited

U.S. PATENT DOCUMENTS

| | | | | |
|---|---|---|---|---|
| 5,064,941 | A * | 11/1991 | Davison | C07K 14/78 530/356 |
| 6,322,785 | B1 | 11/2001 | Landesberg et al. | |
| 2002/0054901 | A1 | 5/2002 | Gainey et al. | |
| 2009/0054350 | A1* | 2/2009 | Tayot | C07K 14/78 514/6.9 |
| 2009/0254104 | A1 | 10/2009 | Murray | |
| 2012/0201897 | A1 | 8/2012 | Park et al. | |

FOREIGN PATENT DOCUMENTS

| | | |
|---|---|---|
| CN | 102573943 | 7/2012 |
| EP | 0322249 | 6/1989 |
| WO | WO 2014/147622 | 9/2014 |

OTHER PUBLICATIONS

Parenteau-Bareil et al. Collagen-based biomaterials for tissue engineering applications. Materials. 2010;3:1863-1887.*
Grant et al. Tuning the elastic modulus of hydrated collagen fibrils. Biophysical Journal. 2009;97:2985-2992.*
Cheng et al. Platelets and plasma proteins are both required to stimulate collagen gene expression by anterior cruciate ligament cells in three-dimensional culture. Tissue Engineering: Part A. 2010;16(5):1479-1489.*
Translation of Notification of Office Action dated Nov. 7, 2017 From the State Intellectual Property Office of the People's Republic of China Re. Application No. 201480025801.1. (13 Pages).
Office Action dated Apr. 23, 2018 From the Israel Patent Office Re. Application No. 241703 and Its Translation Into English. (7 Pages).
Notification of Office Action and Search Report dated Oct. 11, 2016 From the State Intellectual Property Office of the People's Republic of China Re. Application No. 201480025801.1 and Its Translation of Office Action Into English.
Cornwell et al. "Crosslinking of Discrete Self-Assembled Collagen Threads: Effects on Mechanical Strength and Cell-Matrix Interactions", Journal of Biomedical Materials Research Part A, 80(2): 362-371, Published Online Sep. 25, 2006.
Fufa et al. "Activation of Platelet-Rich Plasma Using Soluble Type I Collagen", Journal of Oral and Maxillofacial Surgery, 66(4): 684-690, Apr. 30, 2008.
Haaparanta et al. "The Effect of Cross-Linking Time on A Porous Freeze-Dried Collagen Scaffold Using 1-Ethyl-3-(3-Dimethylaminopropyl)Carbodiimide as A Cross-Linker", Journal of Applied Biomaterials & & Biomechanics, 6(2): 89-94, May 31, 2008.
Harrison et al. "Platelet Activation by Collagen Provides Sustained Release of Anabolic Cytokines", The American Journal of Sports Medicine, 39(4): 729-734, Apr. 2011.
Morton et al. "Integrin Alpha2Beta1-Independent Activation of Platelets by Simple Collagen-Like Peptides: Collagen Tertiary (Triple-Helical) and Quaternary (Polymeric) Structures Are Sufficient Alone for Alpha2Beta1-Independent Platelet Reactivity", Biochemical Journal, 306(Pt.2): 337-344, Mar. 1, 1995.
Notification of Office Action dated Nov. 7, 2017 From the State Intellectual Property Office of the People's Republic of China Re. Application No. 201480025801.1. (9 Pages).
Translation of Notification of Office Action dated May 25, 2017 From the State Intellectual Property Office of the People's Republic of China Re. Application No. 201480025801.1. (13 Pages).
Communication Pursuant to Article 94(3) EPC dated Oct. 2, 2017 From the European Patent Office Re. Application No. 14717487.4. (4 Pages).
International Preliminary Report on Patentability dated Oct. 1, 2015 From the International Bureau of WIPO Re. Application. No. PCT/IL2014/050302.

(Continued)

*Primary Examiner* — Lynn Y Fan

(57) ABSTRACT

A composition of matter is disclosed which comprises crosslinked collagen, platelet rich plasma (PRP) and an inorganic salt. Methods of generating same and uses thereof are also disclosed.

6 Claims, 8 Drawing Sheets
(3 of 8 Drawing Sheet(s) Filed in Color)

Specification includes a Sequence Listing.

(56) References Cited

OTHER PUBLICATIONS

International Search Report and the Written Opinion dated Jun. 20, 2014 From the International Searching Authority Re. Application No. PCT/IL2014/050302.
Lacci et al. "Platelet-Rich Plasma: Support for Its Use in Wound Healing", Yale Journal of Biology and Medicine, 83: 1-9, 2010.
Nimni et al. "Chemically Modified Collagen: A Natural Biomaterial for Tissue Replacement", Journal of Biomedical Materials Research, XP000677234, 21(6): 741-771, Jun. 1, 1987. p. 741-742, 766-767.
Notification of Office Action dated May 25, 2017 From the State Intellectual Property Office of the People's Republic of China Re. Application No. 201480025801.1 and Its Summary Into English. (11 Pages).
Communication Pursuant to Article 94(3) EPC dated Dec. 17, 2018 From the European Patent Office Re. Application No. 14717487.4. (4 Pages).
Notification of Office Action dated Jun. 29, 2018 From the State Intellectual Property Office of the People's Republic of China Re. Application No. 201480025801.1 and Its Translation Into English. (22 Pages).
Cui Fuzhai et al. "Genetic Material", Chemical Industry Press (1): 105-106, Published on Jul. 2004.
Examination Report Under Sections 12 & 13 of the Patents Act, 1977 and the Patents Rules, 2003 dated Feb. 12, 2019 From the Government of India, Intellectual Property India, Patents, Designs, Trade Marks, Geographical Indications Re. Application No. 2802/MUMNP/2015. (6 Pages).
Office Action dated Mar. 3, 2019 From the Israel Patent Office Re. Application No. 241703 and Its Translation Into English. (4 Pages).

* cited by examiner

SEQUENCE LISTING

```
<160> NUMBER OF SEQ ID NOS: 5

<210> SEQ ID NO 1
<211> LENGTH: 1464
<212> TYPE: PRT
<213> ORGANISM: Homo sapiens

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140
```

-continued

```
Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560
```

-continued

```
Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975
```

-continued

```
Gly Pro Ser Gly Glu Pro Gly Lys Gln Gly Pro Ser Gly Ala Ser Gly
            980                 985                 990

Glu Arg Gly Pro Pro Gly Pro Met  Gly Pro Pro Gly Leu  Ala Gly Pro
        995                 1000                1005

Pro Gly  Glu Ser Gly Arg Glu  Gly Ala Pro Gly Ala  Glu Gly Ser
    1010                 1015                 1020

Pro Gly  Arg Asp Gly Ser Pro  Gly Ala Lys Gly Asp  Arg Gly Glu
    1025                 1030                 1035

Thr Gly  Pro Ala Gly Pro Pro  Gly Ala Pro Gly Ala  Pro Gly Ala
    1040                 1045                 1050

Pro Gly  Pro Val Gly Pro Ala  Gly Lys Ser Gly Asp  Arg Gly Glu
    1055                 1060                 1065

Thr Gly  Pro Ala Gly Pro Ala  Gly Pro Val Gly Pro  Val Gly Ala
    1070                 1075                 1080

Arg Gly  Pro Ala Gly Pro Gln  Gly Pro Arg Gly Asp  Lys Gly Glu
    1085                 1090                 1095

Thr Gly  Glu Gln Gly Asp Arg  Gly Ile Lys Gly His  Arg Gly Phe
    1100                 1105                 1110

Ser Gly  Leu Gln Gly Pro Pro  Gly Pro Pro Gly Ser  Pro Gly Glu
    1115                 1120                 1125

Gln Gly  Pro Ser Gly Ala Ser  Gly Pro Ala Gly Pro  Arg Gly Pro
    1130                 1135                 1140

Pro Gly  Ser Ala Gly Ala Pro  Gly Lys Asp Gly Leu  Asn Gly Leu
    1145                 1150                 1155

Pro Gly  Pro Ile Gly Pro Pro  Gly Pro Arg Gly Arg  Thr Gly Asp
    1160                 1165                 1170

Ala Gly  Pro Val Gly Pro Pro  Gly Pro Pro Gly Pro  Pro Gly Pro
    1175                 1180                 1185

Pro Gly  Pro Pro Ser Ala Gly  Phe Asp Phe Ser Phe  Leu Pro Gln
    1190                 1195                 1200

Pro Pro  Gln Glu Lys Ala His  Asp Gly Gly Arg Tyr  Tyr Arg Ala
    1205                 1210                 1215

Asp Asp  Ala Asn Val Val Arg  Asp Arg Asp Leu Glu  Val Asp Thr
    1220                 1225                 1230

Thr Leu  Lys Ser Leu Ser Gln  Gln Ile Glu Asn Ile  Arg Ser Pro
    1235                 1240                 1245

Glu Gly  Ser Arg Lys Asn Pro  Ala Arg Thr Cys Arg  Asp Leu Lys
    1250                 1255                 1260

Met Cys  His Ser Asp Trp Lys  Ser Gly Glu Tyr Trp  Ile Asp Pro
    1265                 1270                 1275

Asn Gln  Gly Cys Asn Leu Asp  Ala Ile Lys Val Phe  Cys Asn Met
    1280                 1285                 1290

Glu Thr  Gly Glu Thr Cys Val  Tyr Pro Thr Gln Pro  Ser Val Ala
    1295                 1300                 1305

Gln Lys  Asn Trp Tyr Ile Ser  Lys Asn Pro Lys Asp  Lys Arg His
    1310                 1315                 1320

Val Trp  Phe Gly Glu Ser Met  Thr Asp Gly Phe Gln  Phe Glu Tyr
    1325                 1330                 1335

Gly Gly  Gln Gly Ser Asp Pro  Ala Asp Val Ala Ile  Gln Leu Thr
    1340                 1345                 1350

Phe Leu  Arg Leu Met Ser Thr  Glu Ala Ser Gln Asn  Ile Thr Tyr
    1355                 1360                 1365
```

-continued

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 2
<211> LENGTH: 1366
<212> TYPE: PRT
<213> ORGANISM: Homo sapiens

<400> SEQUENCE: 2

Met Leu Ser Phe Val Asp Thr Arg Thr Leu Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270

-continued

```
Ala Gly Pro Ala Gly Pro Ala Gly Pro Arg Gly Glu Val Gly Leu Pro
        275                 280                 285

Gly Leu Ser Gly Pro Val Gly Pro Pro Gly Asn Pro Gly Ala Asn Gly
    290                 295                 300

Leu Thr Gly Ala Lys Gly Ala Ala Gly Leu Pro Gly Val Ala Gly Ala
305                 310                 315                 320

Pro Gly Leu Pro Gly Pro Arg Gly Ile Pro Gly Pro Val Gly Ala Ala
                325                 330                 335

Gly Ala Thr Gly Ala Arg Gly Leu Val Gly Glu Pro Gly Pro Ala Gly
            340                 345                 350

Ser Lys Gly Glu Ser Gly Asn Lys Gly Glu Pro Gly Ser Ala Gly Pro
        355                 360                 365

Gln Gly Pro Pro Gly Pro Ser Gly Glu Glu Gly Lys Arg Gly Pro Asn
    370                 375                 380

Gly Glu Ala Gly Ser Ala Gly Pro Pro Gly Pro Pro Gly Leu Arg Gly
385                 390                 395                 400

Ser Pro Gly Ser Arg Gly Leu Pro Gly Ala Asp Gly Arg Ala Gly Val
                405                 410                 415

Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
    450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
                485                 490                 495

Pro Lys Gly Pro Thr Gly Asp Pro Gly Lys Asn Gly Asp Lys Gly His
            500                 505                 510

Ala Gly Leu Ala Gly Ala Arg Gly Ala Pro Gly Pro Asp Gly Asn Asn
        515                 520                 525

Gly Ala Gln Gly Pro Pro Gly Pro Gln Gly Val Gln Gly Gly Lys Gly
    530                 535                 540

Glu Gln Gly Pro Ala Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
                565                 570                 575

Gly Glu Phe Gly Leu Pro Gly Pro Ala Gly Pro Arg Gly Glu Arg Gly
            580                 585                 590

Pro Pro Gly Glu Ser Gly Ala Ala Gly Pro Thr Gly Pro Ile Gly Ser
        595                 600                 605

Arg Gly Pro Ser Gly Pro Pro Gly Pro Asp Gly Asn Lys Gly Glu Pro
    610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
                645                 650                 655

Lys Gly Glu Pro Gly Leu Arg Gly Glu Ile Gly Asn Pro Gly Arg Asp
            660                 665                 670

Gly Ala Arg Gly Ala Pro Gly Ala Val Gly Ala Pro Gly Pro Ala Gly
        675                 680                 685
```

-continued

```
Ala Thr Gly Asp Arg Gly Glu Ala Gly Ala Ala Gly Pro Ala Gly Pro
    690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
                725                 730                 735

Ala Lys Gly Glu Arg Gly Ala Lys Gly Pro Lys Gly Glu Asn Gly Val
            740                 745                 750

Val Gly Pro Thr Gly Pro Val Gly Ala Ala Gly Pro Ala Gly Pro Asn
        755                 760                 765

Gly Pro Pro Gly Pro Ala Gly Ser Arg Gly Asp Gly Gly Pro Pro Gly
    770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
                805                 810                 815

Gly Leu Arg Gly Pro Arg Gly Asp Gln Gly Pro Val Gly Arg Thr Gly
            820                 825                 830

Glu Val Gly Ala Val Gly Pro Pro Gly Phe Ala Gly Glu Lys Gly Pro
        835                 840                 845

Ser Gly Glu Ala Gly Thr Ala Gly Pro Pro Gly Thr Pro Gly Pro Gln
    850                 855                 860

Gly Leu Leu Gly Ala Pro Gly Ile Leu Gly Leu Pro Gly Ser Arg Gly
865                 870                 875                 880

Glu Arg Gly Leu Pro Gly Val Ala Gly Ala Val Gly Glu Pro Gly Pro
                885                 890                 895

Leu Gly Ile Ala Gly Pro Pro Gly Ala Arg Gly Pro Pro Gly Ala Val
            900                 905                 910

Gly Ser Pro Gly Val Asn Gly Ala Pro Gly Glu Ala Gly Arg Asp Gly
        915                 920                 925

Asn Pro Gly Asn Asp Gly Pro Pro Gly Arg Asp Gly Gln Pro Gly His
    930                 935                 940

Lys Gly Glu Arg Gly Tyr Pro Gly Asn Ile Gly Pro Val Gly Ala Ala
945                 950                 955                 960

Gly Ala Pro Gly Pro His Gly Pro Val Gly Pro Ala Gly Lys His Gly
                965                 970                 975

Asn Arg Gly Glu Thr Gly Pro Ser Gly Pro Val Gly Pro Ala Gly Ala
            980                 985                 990

Val Gly Pro Arg Gly Pro Ser Gly  Pro Gln Gly Ile Arg  Gly Asp Lys
        995                 1000                1005

Gly Glu  Pro Gly Glu Lys Gly  Pro Arg Gly Leu Pro  Gly Leu Lys
    1010                1015                1020

Gly His  Asn Gly Leu Gln Gly  Leu Pro Gly Ile Ala  Gly His His
    1025                1030                1035

Gly Asp  Gln Gly Ala Pro Gly  Ser Val Gly Pro Ala  Gly Pro Arg
    1040                1045                1050

Gly Pro  Ala Gly Pro Ser Gly  Pro Ala Gly Lys Asp  Gly Arg Thr
    1055                1060                1065

Gly His  Pro Gly Thr Val Gly  Pro Ala Gly Ile Arg  Gly Pro Gln
    1070                1075                1080

Gly His  Gln Gly Pro Ala Gly  Pro Pro Gly Pro Pro  Gly Pro Pro
    1085                1090                1095

Gly Pro  Pro Gly Val Ser Gly  Gly Gly Tyr Asp Phe  Gly Tyr Asp
    1100                1105                1110
```

-continued

```
Gly Asp  Phe Tyr Arg Ala Asp  Gln Pro Arg Ser Ala  Pro Ser Leu
    1115                 1120                 1125

Arg Pro  Lys Asp Tyr Glu Val  Asp Ala Thr Leu Lys  Ser Leu Asn
    1130                 1135                 1140

Asn Gln  Ile Glu Thr Leu Leu  Thr Pro Glu Gly Ser  Arg Lys Asn
    1145                 1150                 1155

Pro Ala  Arg Thr Cys Arg Asp  Leu Arg Leu Ser His  Pro Glu Trp
    1160                 1165                 1170

Ser Ser  Gly Tyr Tyr Trp Ile  Asp Pro Asn Gln Gly  Cys Thr Met
    1175                 1180                 1185

Asp Ala  Ile Lys Val Tyr Cys  Asp Phe Ser Thr Gly  Glu Thr Cys
    1190                 1195                 1200

Ile Arg  Ala Gln Pro Glu Asn  Ile Pro Ala Lys Asn  Trp Tyr Arg
    1205                 1210                 1215

Ser Ser  Lys Asp Lys Lys His  Val Trp Leu Gly Glu  Thr Ile Asn
    1220                 1225                 1230

Ala Gly  Ser Gln Phe Glu Tyr  Asn Val Glu Gly Val  Thr Ser Lys
    1235                 1240                 1245

Glu Met  Ala Thr Gln Leu Ala  Phe Met Arg Leu Leu  Ala Asn Tyr
    1250                 1255                 1260

Ala Ser  Gln Asn Ile Thr Tyr  His Cys Lys Asn Ser  Ile Ala Tyr
    1265                 1270                 1275

Met Asp  Glu Glu Thr Gly Asn  Leu Lys Lys Ala Val  Ile Leu Gln
    1280                 1285                 1290

Gly Ser  Asn Asp Val Glu Leu  Val Ala Glu Gly Asn  Ser Arg Phe
    1295                 1300                 1305

Thr Tyr  Thr Val Leu Val Asp  Gly Cys Ser Lys Lys  Thr Asn Glu
    1310                 1315                 1320

Trp Gly  Lys Thr Ile Ile Glu  Tyr Lys Thr Asn Lys  Pro Ser Arg
    1325                 1330                 1335

Leu Pro  Phe Leu Asp Ile Ala  Pro Leu Asp Ile Gly  Gly Ala Asp
    1340                 1345                 1350

Gln Glu  Phe Phe Val Asp Ile  Gly Pro Val Cys Phe  Lys
    1355                 1360                 1365


<210> SEQ ID NO 3
<211> LENGTH: 1633
<212> TYPE: DNA
<213> ORGANISM: Artificial sequence
<220> FEATURE:
<223> OTHER INFORMATION: Synthetic sequence containing the coding
      regions of the vascular signal sequence of barley gene for Thiol
      protease aleurain precursor fused to the human Prolyl 4-
      hydroxylase beta subunit and flanking regions

<400> SEQUENCE: 3

ctcgagtaaa ccatggctca tgctagggtt ttgcttttgg ctcttgctgt tcttgctact     60

gctgctgttg ctgtggcttc ttcttcatct ttcgctgatt ctaacccaat taggccagtg    120

actgatagag ctgcttctac tcttgctcaa ttggtcgaca tggatgctcc agaagaggag    180

gatcacgttc ttgtgcttag gaagtctaac ttcgctgaag ctcttgctgc tcacaagtac    240

cttcttgtgg agttttatgc tccttggtgc ggacattgca aagctcttgc tccagagtat    300

gctaaggctg ctggaaagtt gaaggctgag ggatctgaaa ttaggcttgc taaagtggat    360

gctactgagg agtctgatct tgctcaacag tacggagtta ggggataccc aactattaag    420

ttcttcagga acggagatac tgcttctcca aaggagtata ctgctggaag ggaggctgat    480
```

-continued gatattgtga actggcttaa gaagagaact ggaccagctg ctactactct tccagatgga 540
gctgctgctg aatctcttgt ggagtcatct gaggtggcag tgattggatt cttcaaggat 600
gtggagtctg attctgctaa gcagttcctt caagctgctg aggctattga tgatattcca 660
ttcggaatta cttctaactc tgatgtgttc tctaagtacc agcttgataa ggatggagtg 720
gtgcttttca agaaattcga tgagggaagg aacaatttcg agggagaggt gacaaaggag 780
aaccttcttg atttcattaa gcacaaccag cttccacttg tgattgagtt cactgagcag 840
actgctccaa agattttcgg aggagagatt aagactcaca ttcttctttt ccttccaaag 900
tctgtgtctg attacgatgg aaagttgtct aacttcaaga ctgctgctga gtctttcaag 960
ggaaagattc ttttcatttt cattgattct gatcacactg ataaccagag gattcttgag 1020
ttcttcggac ttaagaagga agagtgccca gctgttaggc ttattactct tgaggaggag 1080
atgactaagt acaagccaga gtctgaagaa cttactgctg agaggattac tgagttctgc 1140
cacagattcc ttgagggaaa gattaagcca caccttatgt ctcaagagct tccagaggat 1200
tgggataagc agccagttaa ggtgttggtg ggtaaaaact tcgaggatgt ggctttcgat 1260
gagaagaaga acgtgttcgt ggagttctac gcaccttggt gtggtcactg taagcagctt 1320
gctccaattt gggataagtt gggagagact tacaaggatc acgagaacat tgtgattgct 1380
aagatggatt ctactgctaa cgaggtggag gctgttaagg ttcactcttt cccaactttg 1440
aagttcttcc cagcttctgc tgataggact gtgattgatt acaacggaga aaggactctt 1500
gatggattca agaagttcct tgagtctgga ggacaagatg gagctggaga tgatgatgat 1560
cttgaggatt tggaagaagc tgaggagcca gatatggagg aggatgatga tcagaaggct 1620
gtgtgatgag ctc 1633

<210> SEQ ID NO 4
<211> LENGTH: 1723
<212> TYPE: DNA
<213> ORGANISM: Artificial sequence
<220> FEATURE:
<223> OTHER INFORMATION: Synthetic sequence containing the coding regions of the vascular signal sequence of barley gene for Thiol protease aleurain precursor fused to the human Prolyl 4-hydroxylase alpha-1 subunit and flanking regions

<400> SEQUENCE: 4
ctcgagtaaa ccatggctca tgctagggtt ttgcttttgg ctcttgctgt tcttgctact 60
gctgctgttg ctgtggcttc ttcttcatct ttcgctgatt ctaacccaat taggccagtg 120
actgatagag ctgcttctac tcttgctcaa ttggtcgaca tgcacccagg attcttcact 180
tctattggac agatgactga tcttattcac actgagaagg atcttgtgac ttctcttaag 240
gattacatta aggctgagga ggataagttg gagcagatta agaagtgggc tgagaagttg 300
gataggctta cttctactgc tacaaaagat ccagagggat tcgttggtca tccagtgaac 360
gctttcaagt tgatgaagag gcttaacact gagtggagtg agcttgagaa ccttgtgctt 420
aaggatatgt ctgatggatt catttctaac cttactattc agaggcagta cttcccaaat 480
gatgaggatc aagtgggagc tgctaaggct cttcttaggc ttcaggatac ttacaacctt 540
gatactgata caatttctaa gggaaacctt ccaggagtta agcacaagtc tttccttact 600
gctgaggatt gcttcgagct tggaaaggtt gcatacactg aggctgatta ctaccacact 660
gagctttgga tggaacaagc tcttaggcaa cttgatgagg gagagatttc tactattgat 720
aaggtgtcag tgcttgatta cctttcttac gctgtgtacc agcagggtga tcttgataag 780

-continued

```
gctcttttgc ttactaagaa gttgcttgag cttgatccag aacatcagag ggctaacgga    840

aaccttaagt acttcgagta cattatggct aaggaaaagg atgtgaacaa gtctgcttct    900

gatgatcagt ctgatcaaaa gactactcca aagaagaagg gagtggctgt tgattatctt    960

cctgagaggc agaagtatga gatgttgtgt aggggagagg gtattaagat gactccaagg   1020

aggcagaaga agttgttctg caggtatcac gatggaaaca ggaacccaaa gttcattctt   1080

gctccagcta agcaagaaga tgagtgggat aagccaagga ttattaggtt ccacgatatt   1140

atttctgatg ctgagattga gattgtgaag gatcttgcta agccaagact taggagggct   1200

actatttcta accctattac tggtgatctt gagactgtgc actacaggat ttctaagtct   1260

gcttggcttt ctggatacga gaacccagtg gtgtctagga ttaacatgag gattcaggat   1320

cttactggac ttgatgtgtc tactgctgag gagcttcaag ttgctaacta cggagttgga   1380

ggacaatatg agccacactt cgatttcgct aggaaggatg agccagatgc ttttaaggag   1440

cttggaactg gaaacaggat tgctacttgg cttttctaca tgtctgatgt ttctgctgga   1500

ggagctactg ttttcccaga agtgggagct tctgtttggc caaagaaggg aactgctgtg   1560

ttctggtaca accttttcgc ttctggagag ggagattact ctactaggca tgctgcttgc   1620

ccagttcttg ttggaaacaa gtgggtgtca aacaagtggc ttcatgagag gggacaagag   1680

tttagaaggc catgcactct ttctgagctt gagtgatgag ctc                     1723
```

<210> SEQ ID NO 5
<211> LENGTH: 2888
<212> TYPE: DNA
<213> ORGANISM: Artificial sequence
<220> FEATURE:
<223> OTHER INFORMATION: Synthetic sequence containing the coding regions of the vascular signal sequence of barley gene for Thiol protease aleurain precursor fused to the human Lysyl hydroxylase 3 and flanking regions

<400> SEQUENCE: 5

```
gcgaattcgc tagctatcac tgaaaagaca gcaagacaat ggtgtctcga tgcaccagaa     60

ccacatcttt gcagcagatg tgaagcagcc agagtggtcc acaagacgca ctcagaaaag    120

gcatcttcta ccgacacaga aaaagacaac cacagctcat catccaacat gtagactgtc    180

gttatgcgtc ggctgaagat aagactgacc ccaggccagc actaaagaag aaataatgca    240

agtggtccta gctccacttt agctttaata attatgtttc attattattc tctgcttttg    300

ctctctatat aaagagcttg tattttcatt tgaaggcaga ggcgaacaca cacacagaac    360

ctccctgctt acaaaccaga tcttaaacca tggctcacgc tagggttttg cttcttgctc    420

ttgctgttct tgctactgct gctgttgctg tggcttcttc aagttctttc gctgattcta    480

acccaattag gccagtgact gatagagctg cttctactct tgctcaattg agatctatgt    540

ctgatagacc aaggggaagg gatccagtta atccagagaa gttgcttgtg attactgtgg    600

ctactgctga gactgaagga taccttagat tccttaggag tgctgagttc ttcaactaca    660

ctgtgaggac tcttggactt ggagaagaat ggaggggagg agatgttgct agaactgttg    720

gaggaggaca gaaagtgaga tggcttaaga aagagatgga gaagtacgct gatagggagg    780

atatgattat tatgttcgtg gattcttacg atgtgattct tgctggatct ccaactgagc    840

ttttgaagaa attcgttcag tctggatcta ggcttctttt ctctgctgag tctttttgtt    900

ggccagaatg ggacttgct gagcaatatc cagaagtggg aactggaaag agattcctta    960

actctggagg attcattgga ttcgctacta ctattcacca gattgtgagg cagtggaagt   1020
```

-continued

```
acaaggatga cgatgatgat cagcttttct acactaggct ttaccttgat ccaggactta   1080
gggagaagtt gtctcttaac cttgatcaca agtctaggat tttccagaac cttaacggtg   1140
ctcttgatga ggttgtgctt aagttcgata ggaacagagt gaggattagg aacgtggctt   1200
acgatactct tcctattgtg gtgcatggaa acggaccaac aaaactccag cttaactacc   1260
ttggaaacta cgttccaaac ggatggactc cagaaggagg atgtggattc tgcaatcagg   1320
ataggagaac tcttccagga ggacaaccac caccaagagt tttccttgct gtgttcgttg   1380
aacagccaac tccattcctt ccaagattcc ttcagaggct tcttcttttg gattacccac   1440
cagatagggt gacacttttc cttcacaaca acgaggtttt ccacgagcca cacattgctg   1500
attcttggcc acagcttcag gatcatttct ctgctgtgaa gttggttggt ccagaagaag   1560
ctctttctcc aggagaagct agggatatgg ctatggattt gtgcaggcag gatccagagt   1620
gcgagttcta cttctctctt gatgctgatg ctgtgcttac taaccttcag actcttagga   1680
ttcttattga ggagaacagg aaagtgattg ctccaatgct ttctaggcac ggaaagttgt   1740
ggtctaattt ctggggtgct ctttctcctg atgagtacta cgctagatca gaggactacg   1800
tggagcttgt tcagagaaag agagtgggag tttggaacgt tccttatatt tctcaggctt   1860
acgtgattag gggagatact cttaggatgg agcttccaca gagggatgtt ttctctggat   1920
ctgatactga tccagatatg gctttctgca agtctttcag ggataaggga attttccttc   1980
acctttctaa ccagcatgag ttcggaagat tgcttgctac ttcaagatac gatactgagc   2040
accttcatcc tgatctttgg cagattttcg ataacccagt ggattggaag gagcagtaca   2100
ttcacgagaa ctactctagg gctcttgaag gagaaggaat tgtggagcaa ccatgcccag   2160
atgtttactg gttcccactt ctttctgagc aaatgtgcga tgagcttgtt gctgagatgg   2220
agcattacgg acaatggagt ggaggtagac atgaggattc taggcttgct ggaggatacg   2280
agaacgttcc aactgtggat attcacatga agcaagtggg atacgaggat caatggcttc   2340
agcttcttag gacttatgtg ggaccaatga ctgagtctct ttcccagga taccacacta    2400
aggctagggc tgttatgaac ttcgttgtga ggtatcgtcc agatgagcaa ccatctctta   2460
ggccacacca cgattcttct actttcactc ttaacgtggc tcttaaccac aagggacttg   2520
attatgaggg aggaggatgc cgtttcctta gatacgattg cgtgatttct tcaccaagaa   2580
agggatgggc tcttcttcat ccaggaaggc ttactcatta ccacgaggga cttccaacta   2640
cttggggaac tagatatatt atggtgtctt tcgtggatcc atgactgctt taatgagata   2700
tgcgagacgc ctatgatcgc atgatatttg ctttcaattc tgttgtgcac gttgtaaaaa   2760
acctgagcat gtgtagctca gatccttacc gccggtttcg gttcattcta atgaatatat   2820
cacccgttac tatcgtattt ttatgaataa tattctccgt tcaatttact gattgtccag   2880
aattcgcg                                                            2888
```

COMPOSITIONS COMPRISING COLLAGEN AND PRP FOR TISSUE REGENERATION

RELATED APPLICATIONS

This application is a National Phase of PCT Patent Application No. PCT/IL2014/050302 having International filing date of Mar. 19, 2014, which claims the benefit of priority under 35 USC § 119(e) of U.S. Provisional Patent Application No. 61/803,856 filed on Mar. 21, 2013. The contents of the above applications are all incorporated by reference as if fully set forth herein in their entirety.

SEQUENCE LISTING STATEMENT

The ASCII file, entitled 63548SequenceListing.txt, created on Aug. 9, 2015, comprising 35,143 bytes, submitted concurrently with the filing of this application is incorporated herein by reference.

FIELD AND BACKGROUND OF THE INVENTION

The present invention, in some embodiments thereof, relates to compositions comprising collagen and platelet rich plasma (PRP) for tissue regeneration and, more particularly, but not exclusively, for soft tissue regeneration.

Platelet-rich plasma (PRP) is blood plasma that has been enriched with platelets. As a concentrated source of autologous platelets, PRP contains (and releases through degranulation) several different growth factors and other cytokines that stimulate healing of bone and soft tissue.

PRP functions as a tissue sealant and drug delivery system, with the platelets initiating wound repair by releasing locally acting growth factors via α-granules degranulation. The secretory proteins contained in the α-granules of platelets include platelet-derived growth factor (PDGF-AA, BB, and AB isomers), transforming growth factor-β (TGF-β), platelet factor 4 (PF4), interleukin-1 (IL-1), platelet-derived angiogenesis factor (PDAF), vascular endothelial growth factor (VEGF), epidermal growth factor (EGF), platelet-derived endothelial growth factor (PDEGF), epithelial cell growth factor (ECGF), insulin-like growth factor (IGF), osteocalcin (Oc), osteonectin (On), fibrinogen (Ff), vitronectin (Vn), fibronectin (Fn), and thrombospondin-1 (TSP-1). These growth factors aid healing by attracting un-differentiated cells in the newly formed matrix and triggering cell division. PRP may suppress cytokine release and limit inflammation, interacting with macrophages to improve tissue healing and regeneration, promote new capillary growth, and accelerate epithelialization in chronic wounds.

Platelets in PRP also play a role in host defense mechanism at the wound site by producing signaling proteins that attract macrophages; PRP also may contain a small number of leukocytes that synthesize interleukins as part of a non-specific immune response.

The delivery and residence of PRP into the injury site remains a challenge due to its liquid state and therefore the potential loss of material to the surrounding tissues. Thrombin (mainly bovine-derived) is a common platelet activator that is used for clot formation and increases the gelation of PRP. The use of thrombin has several disadvantages. Thrombin has undesirable immune response in humans. In addition, in-vitro studies have shown inhibition of cell proliferation and viability (Lawson J H. Semin Thromb Hemost, 2006; 32 (Suppl 1) 98-110; Murray M M et al., J Orthop Res. 2007 35(1) p. 81-91).

Type I collagen, which has a native involvement in the intrinsic clotting cascade, is found to be an attractive alternative to thrombin for platelet activation. Besides being the major protein component in mammalian connective tissue, it is the most studied natural scaffold for regenerative medicine and tissue engineering.

Several in-vitro studies investigated the cytokine release from PRP clots activated by thrombin or by collagen in order to characterize their release profile (Tsay R C, et al., J Oral Maxillofac Surg, 2005 63 p. 521-528; Fufa D, et al., J Oral Maxillofac Surg, 2008 66(4) p. 684-690). Type I collagen in various physical states, soluble or fibrillar, was shown to be as effective as thrombin in stimulating release of TGF, PDGF and VEGF over several days. Cultures of activated PRP either by thrombin or type I collagen were incubated for up to 15 days and collagen-based clot was shown to maintain its initial shape and size where the majority of thrombin based clot was degraded.

Laci et al., Yale J Biol Med. 2010 March; 83(1): 1-9 teaches that calcium chloride may be used to activate PRP clots.

U.S. Patent Application No. 20120201897 teaches the combination of calcium chloride and type I collagen for the activation of PRP clots.

SUMMARY OF THE INVENTION

According to an aspect of some embodiments of the present invention there is provided a composition of matter comprising crosslinked collagen, platelet rich plasma (PRP) and an inorganic salt.

According to an aspect of some embodiments of the present invention there is provided a composition of matter comprising collagen, platelet rich plasma (PRP) and an inorganic salt, being capable of releasing more than 4000 pg/ml of platelet derived growth factor (PDGF) following 10 days of incubation at 37° C.

According to an aspect of some embodiments of the present invention there is provided a method of treating a wound or inducing tissue regeneration in a subject in need thereof, comprising administering to the subject a therapeutically effective amount of the composition of matter described herein, thereby treating the wound or inducing tissue regeneration.

According to an aspect of some embodiments of the present invention there is provided a method of producing a composition of matter for treating a wound or inducing regeneration of tissue comprising:

(a) generating a mixture of collagen and inorganic salt; and (b) contacting the mixture with PRP, thereby producing the composition of matter for treating a wound or inducing regeneration of tissue.

According to some embodiments of the invention, the inorganic salt is selected from the group consisting of a sodium salt, chloride salt, potassium salt, calcium salt, magnesium salt, phosphate salt, sulfate salt and a carboxylate salt.

According to some embodiments of the invention, the inorganic salt is selected from the group consisting of NaCl, KCl, CsCl, $CaCl_2$, CsF, $KClO_4$ $NaNO_3$ and $CaSO_4$.

According to some embodiments of the invention, the organic salt is $CaCl_2$.

According to some embodiments of the invention, the composition of matter is in a liquid state.

According to some embodiments of the invention, the composition of matter is in a semi-solid state.

According to some embodiments of the invention, the composition of matter is suturable.

According to some embodiments of the invention, the collagen comprises human collagen.

According to some embodiments of the invention, the collagen comprises type I collagen.

According to some embodiments of the invention, the collagen comprises fibrillated collagen.

According to some embodiments of the invention, the collagen comprises recombinant collagen.

According to some embodiments of the invention, the recombinant collagen is generated in a plant.

According to some embodiments of the invention, the collagen is present at a concentration of about 10-50 mg/ml.

According to some embodiments of the invention, the collagen is present at a concentration of about 20-30 mg/ml.

According to some embodiments of the invention, the calcium chloride is present at a concentration of about 7-60 mM.

According to some embodiments of the invention, the composition of matter is capable of producing a clot at 37° C. in about 6-7 minutes.

According to some embodiments of the invention, the clot is suturable.

According to some embodiments of the invention, the composition is resistant to degradation following 30 days of incubation at 37° C.

According to some embodiments of the invention, the subject has a disease of the tendon or bone.

According to some embodiments of the invention, the tissue is tendon or bone.

According to some embodiments of the invention, the composition of matter is treating a wound or inducing tissue regeneration in a subject.

According to some embodiments of the invention, the inorganic salt is selected from the group consisting of sodium salt, chloride salt, potassium salt, calcium salt, magnesium salt, phosphate salt, sulfate salt and a carboxylate salt.

According to some embodiments of the invention, the inorganic salt is selected from the group consisting of NaCl, KCl, CsCl, $CaCl_2$, CsF, $KClO_4$ $NaNO_3$ and $CaSO_4$.

According to some embodiments of the invention, the method further comprises drying the mixture prior to the contacting.

According to some embodiments of the invention, the collagen is obtained by fibrillating a solution of recombinant collagen.

According to some embodiments of the invention, the method further comprises crosslinking the collagen following the fibrillating.

According to some embodiments of the invention, the drying comprises freeze-drying.

According to some embodiments of the invention, the method further comprises hydrating the mixture following the drying with a hydrating solution prior to the contacting.

According to some embodiments of the invention, the hydrating solution comprises platelet poor plasma (PPP).

According to some embodiments of the invention, the crosslinking is effected by contacting the collagen with EDC or DHT.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
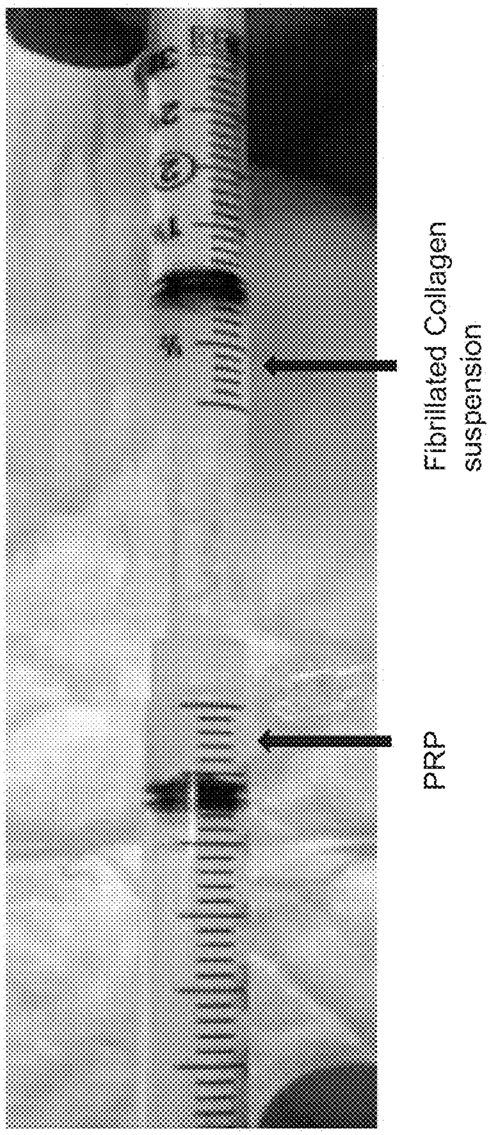

FIG. 1 is a photograph of the set-up of PRP mixing by using two syringes according to an exemplary embodiment of the present invention. One syringe contains a suspension of hydrated collagen. The other syringe contains PRP. The mixing is performed by connecting the two syringes with a luer lock.

FIGS. 2A-D are SEM images of thrombin-PRP based clot (A,B) and rhCollagen-PRP based clot (C,D). Scale-bar 10 μm. Platelet cell elements can be observed forming a cell conglomerate trapped among fibrillar elements (fibrin). The rhCollagen fibers are entrapped within fibrin elements.

Figure 3A:
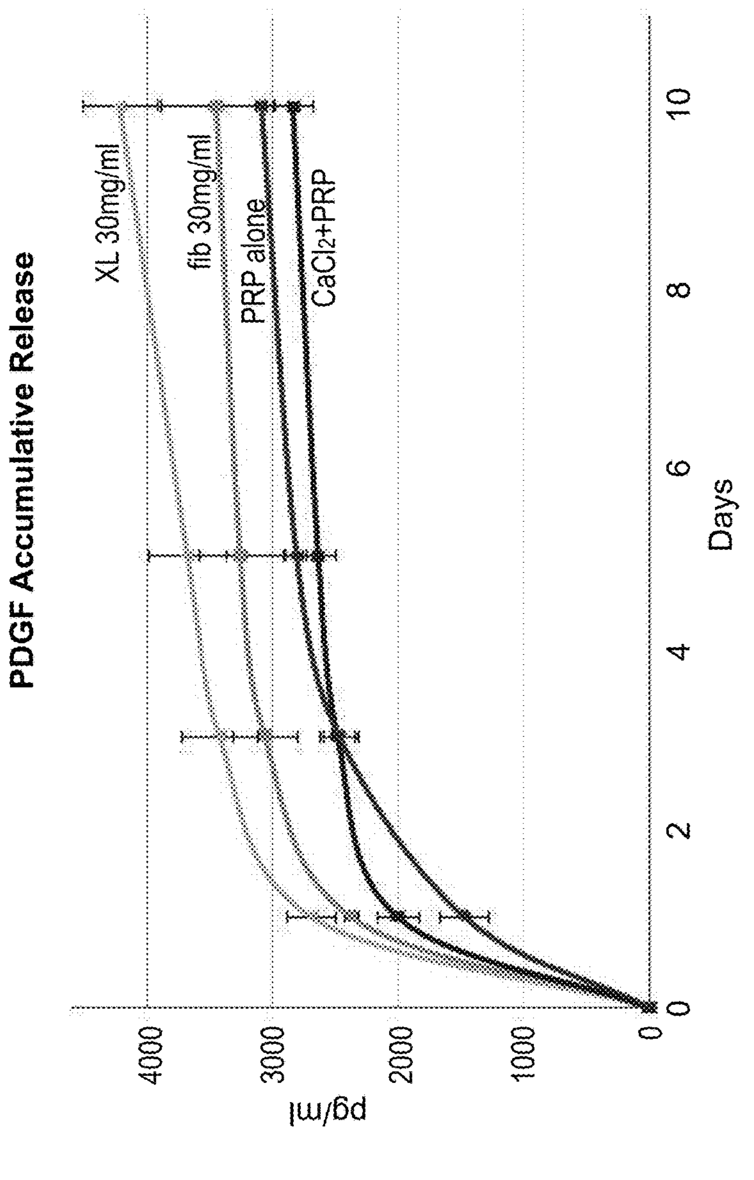
Figure 3B:
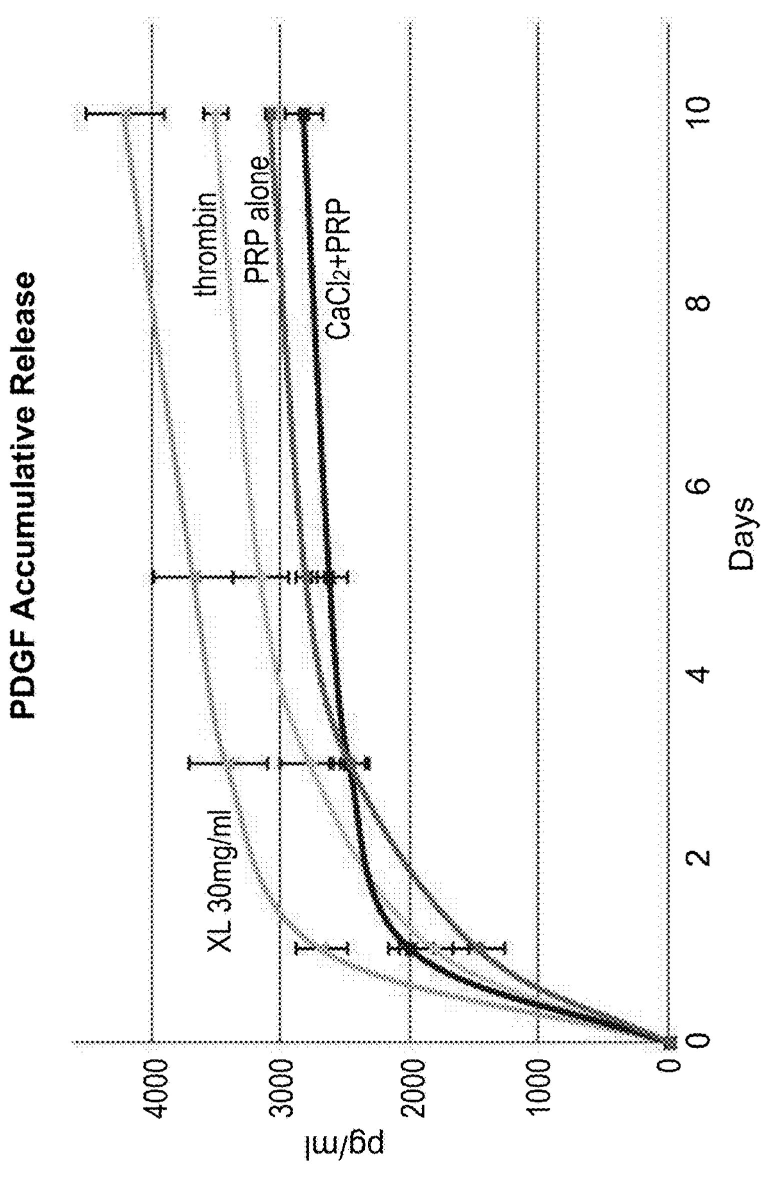

FIGS. 3A-B illustrate an in-vitro accumulative release profile of PDGF growth factor from two types of rhCollagen formulations (cross-linked fibrillated collagen and non-cross-linked fibrillated collagen) relative to activated PRP by $CaCl_2$ and self-activated PRP (A) and 30 mg/ml cross-linked rhCollagen relative to PRP activated by thrombin, activated by $CaCl_2$ and self-activated PRP (B), 10 days following clot formation.

Figure 4:
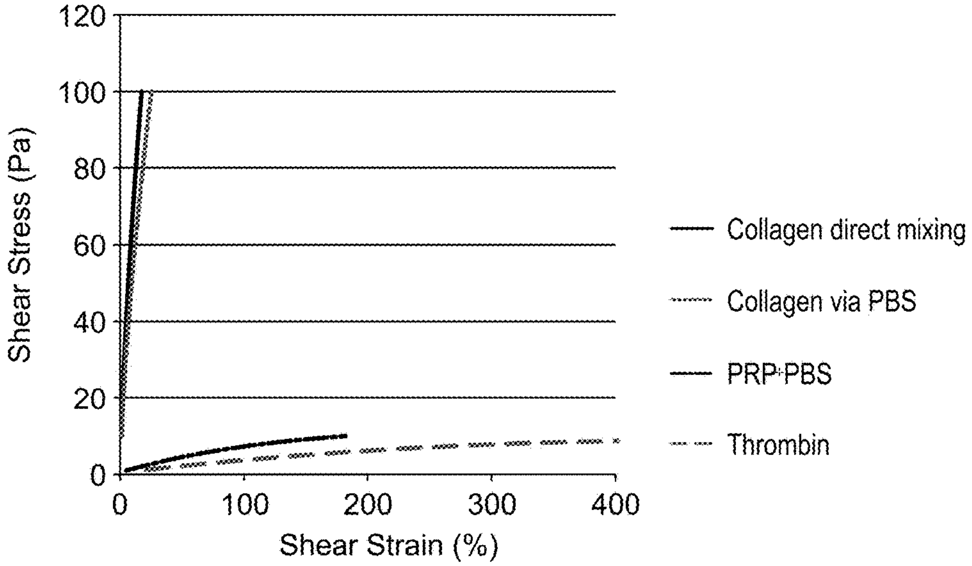

FIG. 4 is a shear stress-strain curve of rhCollagen-based clots compared with controls of thrombin+PRP and PBS+$CaCl_2$+PRP. The two types of rhCollagen based clots were obtained by direct mixing of rhCollagen flakes with $CaCl_2$+PRP (collagen direct mixing) or by hydrating the rhcollagen flakes first with PBS and then mixing with $CaCl_2$+PRP (rhcollagen via PBS).

Figure 5B:
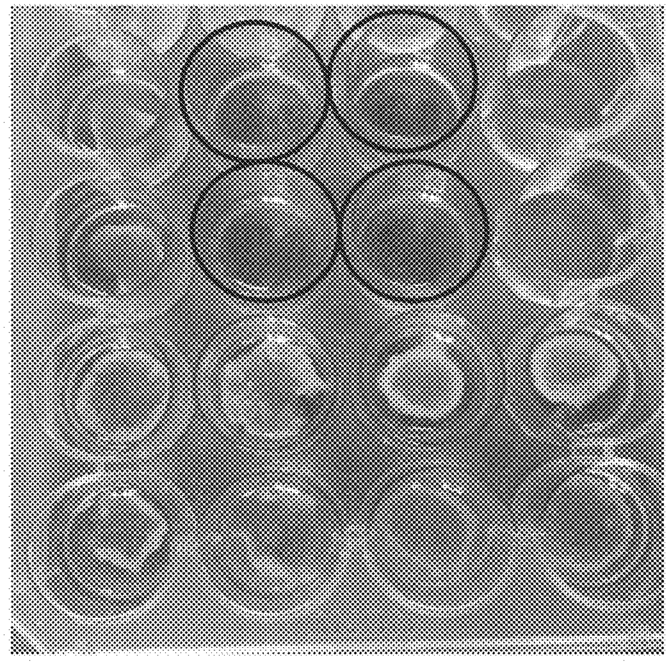
Figure 5A:
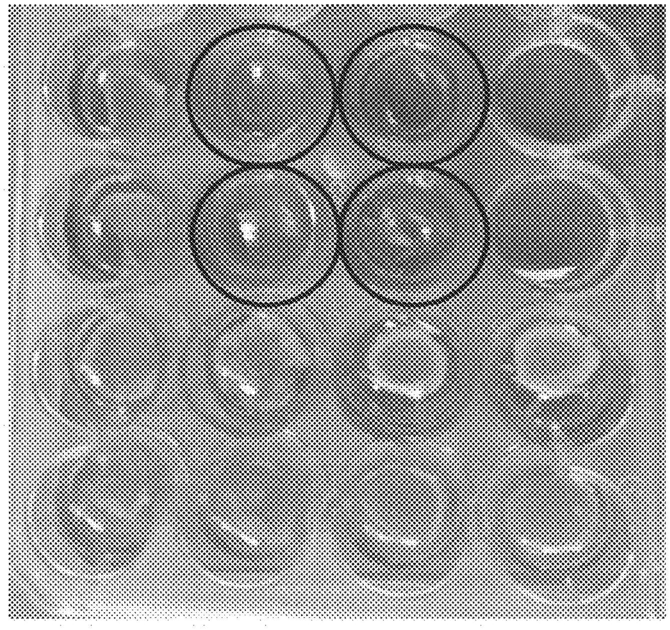

FIGS. 5A-B are photographs illustrating the in-vitro results of a degradation assay of rhCollagen based clots compared with thrombin-based clots (blue circles) after 2 days (FIG. 5A) and 12 days (FIG. 5B). Complete degradation of thrombin-based clots can be clearly observed. rhCollagen based clots remained stable throughout the same period of time.

Figure 6A:
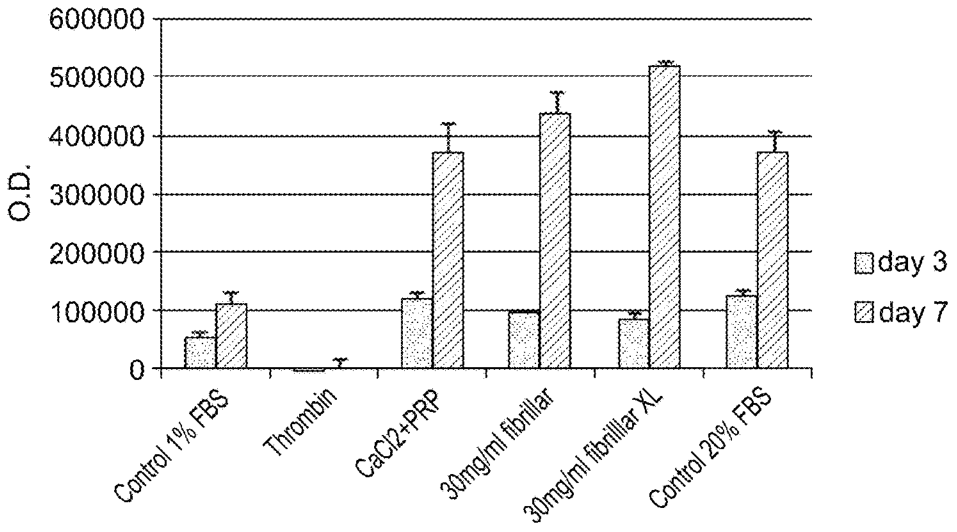
Figure 6B:
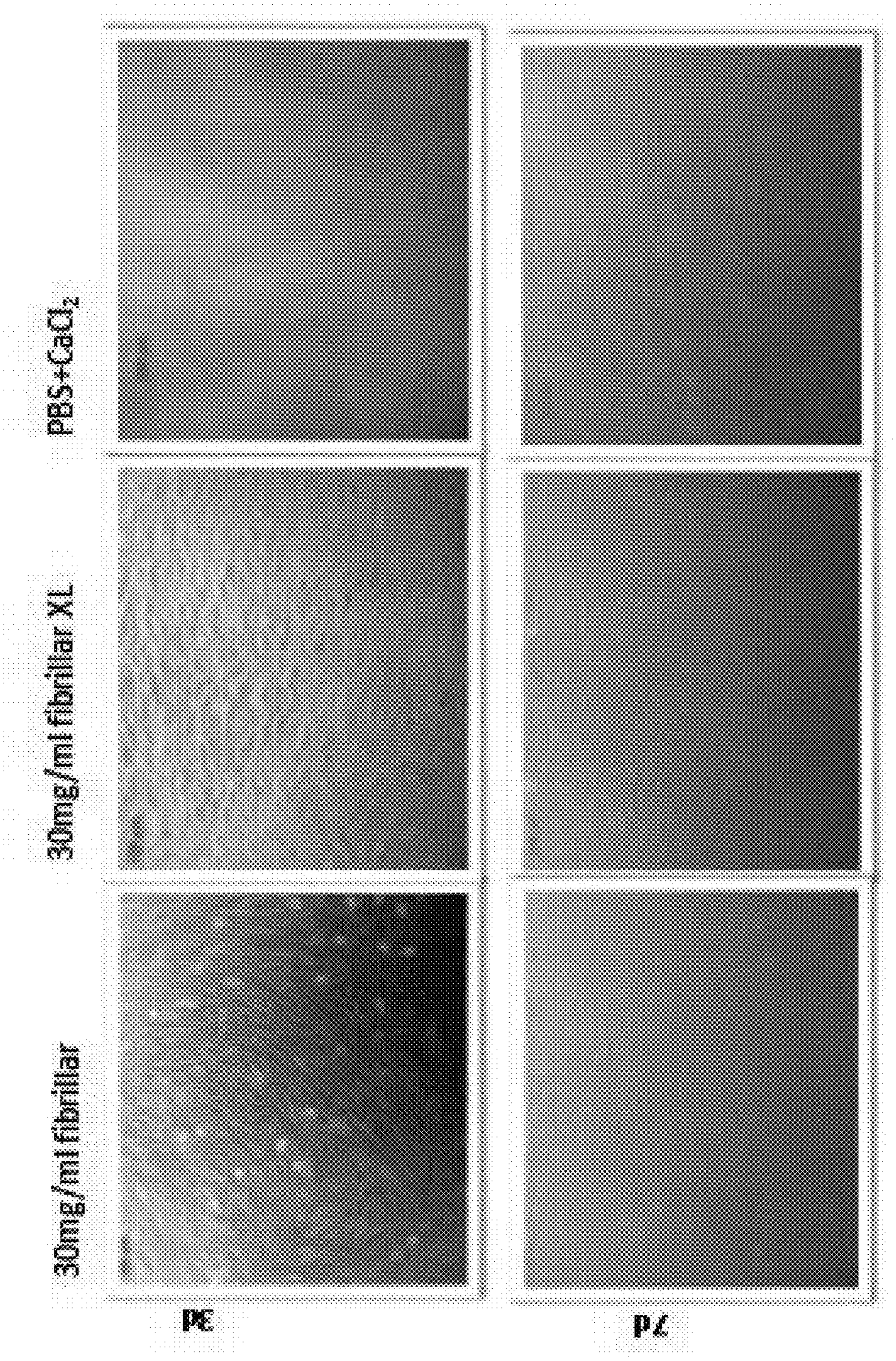

FIGS. 6A-B illustrate the results of a nHDF cell proliferation study 3 and 7 days following seeding. FIG. 6A represents the quantitative proliferation detected by using WST staining. FIG. 6B demonstrates the microscopy of cells that proliferated around the transwell following 3 and 7 days for clot samples of 30 mg/ml fibrillar, 30 mg/ml fibrillar cross-linked collagen and clot that was based on the mixture of $CaCl_2$ with PBS+PRP (devoid of rhcollagen).

DESCRIPTION OF SPECIFIC EMBODIMENTS OF THE INVENTION

The present invention, in some embodiments thereof, relates to compositions comprising collagen and platelet rich plasma (PRP) for tissue regeneration and, more particularly, but not exclusively, for soft tissue regeneration.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

PRP is blood plasma with concentrated platelets. The platelets found in PRP are highly concentrated and comprise growth factors, as well as a large supply of bioactive proteins which are crucial to activate and accelerate tissue repair and regeneration. The bioactive proteins increase the production of stem cells which initiate the healing of connective tissue, regeneration and repair of bones, promotion of new blood vessels and stimulation of the wound healing process.

Application of PRP in a liquid form to a wound site can be complicated by significant loss of the PRP into the surrounding space unless gelation via the clotting mechanism is accomplished. Gelation is currently accomplished using bovine thrombin.

While bovine thrombin is a potent platelet activator, it also causes the development of antibodies against thrombin, prothrombin, factor V, and cardiolipin with resultant clinical problems that range from severe postoperative bleeding to an autoimmune syndrome similar to lupus in animal studies. The use of bovine thrombin also results in impaired migration of fibroblasts through collagen-PRP clots, as well as impaired strength of the clots. In addition, the high degree of retraction seen with thrombin-activated clots makes them difficult for use in wound-space-filling applications.

The present inventors propose the use of collagen as an activator of PRP, whereby the collagen is formulated so as to control the rate of release of growth factors from the clot. For example, the present inventors show that more platelet derived growth factor (PDGF) is released when crosslinked collagen is used to activate the PRP clot as compared to when non-crosslinked collagen is used to activate the PRP clot, as illustrated in FIGS. 3A-B. In addition, the present inventors propose that calcium chloride can be added to the formulation to control the time taken for clot formation.

Figure 2A:
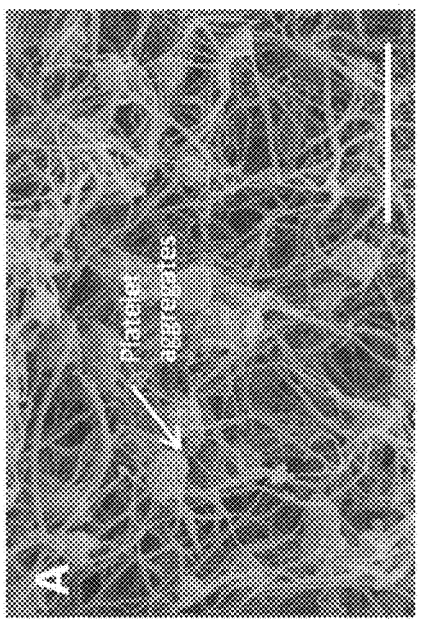
Figure 2B:
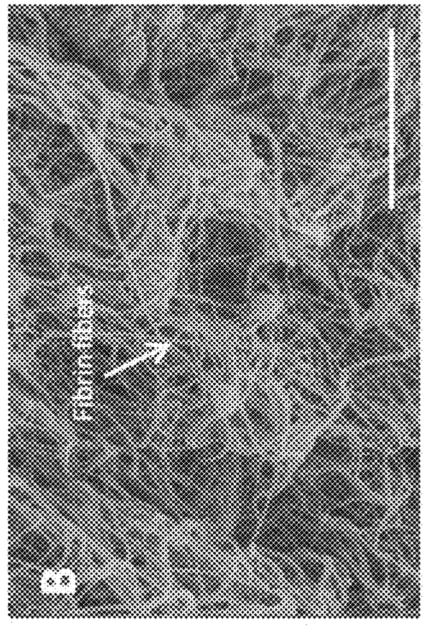

Whilst reducing the present invention to practice, the present inventors have shown that collagen acts as a filler in the PRP clot, whereby the collagen fibers are entrapped within fibrin elements of the clot (FIGS. 2A-B). It is proposed that the ability of the collagen to interconnect between the fibrin elements is responsible for the strength and suturability of the clot.

Thus, according to one aspect of the present invention there is provided a composition of matter comprising cross-linked collagen, platelet rich plasma (PRP) and calcium chloride.

As used herein, the phrase "platelet rich plasma" refers to plasma which has a concentration of platelets greater than in peripheral blood. While normal platelet counts may range from about 140,000 to about 400,000 per microliter, some platelet concentrations of PRP may be in the range of about 500,000 to about 1,200,000 per microliter or more. PRP may be formed from whole blood, and may be obtained using autologous, allogenic, or pooled sources of platelets and/or plasma. PRP may be formed from a variety of animal sources, including human sources.

Typically, PRP may contain 95% platelets with 4% red blood cells and 1% white blood cells.

In some examples, PRP may be further processed, including but not limited to leukoreduction and immunoadsorbtion. Other PRP compositions are further described in U.S. Pat. No. 6,811,777 to Mishra filed Apr. 11, 2003, which is hereby incorporated herein by reference in its entirety.

Whole blood may be drawn from a patient using standard procedures.

The whole blood may or may not be cooled after being collected. Isolation of platelets from whole blood depends upon the density difference between platelets and red blood cells. The platelets and white blood cells are concentrated in the layer (i.e., the "buffy coat") between the platelet depleted plasma (top layer) and red blood cells (bottom layer). For example, a bottom buoy and a top buoy may be used to trap the platelet-rich layer between the upper and lower phase. This platelet-rich layer may then be withdrawn using a syringe or pipette. Generally, at least 60%, at least 70%, or at least 80% of the available platelets within the blood sample can be captured. These platelets may be resuspended in a volume that may be about 3% to about 20% or about 5% to about 10% of the sample volume.

In some examples, the blood may then be centrifuged using a gravitational platelet system, such as the Cell Factor Technologies GPS System® centrifuge. The blood-filled syringe containing between about 20 cc to about 150 cc of blood (e.g., about 55 cc of blood) and about 5 cc citrate dextrose may be slowly transferred to a disposable separation tube which may be loaded into a port on the GPS centrifuge. The sample may be capped and placed into the centrifuge. The samples may then be spun to separate platelets from blood and plasma. The samples may be spun at about 2000 rpm to about 5000 rpm for about 5 minutes to about 30 minutes. For example, centrifugation may be performed at 3200 rpm for extraction from a side of the separation tube and then isolated platelets may be suspended in about 3 cc to about 5 cc of plasma by agitation. The PRP may then be extracted from a side port using, for example, a 10 cc syringe. If about 55 cc of blood may be collected from a patient, about 5 cc of PRP may be obtained.

As the PRP composition comprises activated platelets, active agents within the platelets are released. These agents include, but are not limited to, cytokines (e.g., IL-1B, IL-6, TNF-.alpha.), chemokines (e.g., ENA-78 (CXCL5), IL-8 (CXCL8), MCP-3 (CCL7), MIP-1A (CCL3), NAP-2 (CXCL7), PF4 (CXCL4), RANTES (CCL5)), inflammatory mediators (e.g., PGE2), and growth factors (e.g., Angiopoitin-1, bFGF, EGF, FGF, HGF, IGF-I, IGF-II, PDAF, PDEGF, PDGF AA and BB, TGF-beta 1, 2, and 3, and VEGF).

The term "collagen" as used herein, refers to a polypeptide having a triple helix structure and containing a repeating Gly-X-Y triplet, where X and Y can be any amino acid but are frequently the imino acids proline and hydroxyproline. According to one embodiment, the collagen is a type I, II, III, V, XI, or biologically active fragments therefrom.

A collagen of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to collagen sequences listed in Table 1 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 1 below lists examples of collagen NCBI sequence numbers.

TABLE 1

| Exemplary collagen NCBI sequence number | SEQ ID NO: |
|---|---|
| P02452 | 1 |
| P08123 | 2 |

According to one embodiment, the collagen of the present invention comprises a sufficient portion of its telopeptides such that under suitable conditions it is capable of forming fibrils.

Thus, for example, the collagen may be atelocollagen, a telocollagen or digested procollagen.

As used herein, the term "atelocollagen" refers to collagen molecules lacking both the N- and C-terminal propeptides typically comprised in procollagen, but including a sufficient portion of its telopeptides such that under suitable conditions it is capable of forming fibrils.

The term "procollagen" as used herein, refers to a collagen molecule (e.g. human) that comprises either an N-terminal propeptide, a C-terminal propeptide or both.

The term "telocollagen" as used herein, refers to collagen molecules that lack both the N- and C-terminal propeptides typically comprised in procollagen but still contain the telopeptides. The telopeptides of fibrillar collagen are the remnants of the N- and C-terminal propeptides following digestion with native N/C proteinases.

According to another embodiment, the collagen is a mixture of the types of collagen above.

The collagen may be isolated from an animal (e.g. bovine or pig) or from human cadavers or may be genetically engineered using recombinant DNA technology as further described herein below. According to a specific embodiment, the collagen is devoid of animal-derived (i.e. non-human) collagen.

According to one embodiment, the collagen is recombinant human collagen.

Preferably, the recombinant human collagen is generated in plants.

Below is a description of various methods of obtaining collagen used for the PRP composition described herein.

Methods of isolating collagen from animals are known in the art. Dispersal and solubilization of native animal collagen can be achieved using various proteolytic enzymes (such as porcine mucosal pepsin, bromelain, chymopapain, chymotrypsin, collagenase, ficin, papain, peptidase, proteinase A, proteinase K, trypsin, microbial proteases, and, similar enzymes or combinations of such enzymes) which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121,049; 3,131,130; 3,314,861; 3,530,037; 3,949,073; 4,233,360 and 4,488,911 for general methods for preparing purified soluble collagen). The resulting soluble collagen can be subsequently purified by repeated precipitation at low pH and high ionic strength, followed by washing and re-solublization at low pH.

Plants expressing collagen chains and procollagen are known in the art, see for example, WO06035442A3; Merle et al., FEBS Lett. 2002 Mar. 27; 515(1-3):114-8. PMID: 11943205; and Ruggiero et al., 2000, FEBS Lett. 2000 Mar. 3; 469(1):132-6. PMID: 10708770; and U.S. Pat. Applications 2002/098578 and 2002/0142391 as well as U.S. Pat. No. 6,617,431 each of which are incorporated herein by reference.

It will be appreciated that the present invention also contemplates genetically modified forms of collagen/atelocollagen—for example collagenase-resistant collagens and the like [Wu et al., Proc Natl. Acad Sci, Vol. 87, p. 5888-5892, 1990].

Recombinant collagen may be expressed in any animal or non-animal cell. Examples of non-animal cells include but are not limited to plant cells and other eukaryotic cells such as yeast and fungus. Examples of animal cells include but are not limited to CHO cells and milk.

Plants in which human collagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant procollagen is typically effected by stable or transient transformation with an exogenous polynucleotide sequence encoding human procollagen.

Production of human telocollagen in plants is typically effected by stable or transient transformation with an exogenous polynucleotide sequence encoding human procollagen and at least one exogenous polynucleotide sequence encoding the relevant protease.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes [Olsen et al, Adv Drug Deliv Rev. 2003 Nov. 28; 55(12):1547-67].

Thus, according to one embodiment, the collagen is directed to a subcellular compartment of a plant that is devoid of endogenous P4H activity. As is used herein, the phrase "subcellular compartment devoid of endogenous P4H activity" refers to any compartmentalized region of the cell which does not include plant P4H or an enzyme having plant-like P4H activity.

According to one embodiment, the subcellular compartment is a vacuole.

Accumulation of the expressed collagen in a subcellular compartment devoid of endogenous P4H activity can be effected via any one of several approaches.

For example, the expressed collagen can include a signal sequence for targeting the expressed protein to a subcellular compartment such as the vacuole. Since it is essential that P4H co-accumulates with the expressed collagen chain, the coding sequence thereof is preferably modified accordingly (e.g. by addition or deletion of signal sequences). Thus, P4H is co-expressed with the collagen in the plant, whereby the P4H also includes a signal sequence for targeting to the same subcellular compartment such as the vacuole. Preferably, both the collagen sequence and the P4H sequence are devoid of an endoplasmic reticulum retention signal, such that it passes through the ER and is retained in the vacuole, where it is hydroxylated.

The present invention therefore contemplates genetically modified cells co-expressing both human collagen and a P4H, capable of correctly hydroxylating the collagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a mammalian P4H (e.g. human P4H which is encoded by, for example, SEQ ID Nos: 3 and 4). In addition, P4H mutants which exhibit enhanced substrate specificity, or P4H homologues can also be used.

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. 060568, can catalyze all three consecutive modifying steps as seen in hydroxylysine-linked carbohydrate formation.

Thus, the genetically modified cells of the present invention may also express mammalian LH3. An LH3 encoding sequence such as that set forth by SEQ ID NO: 5, can be used for such purposes.

The collagen and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

There are various methods for introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct, in which case these sequences are not inherited by the plant's progeny.

In addition, several methods exist in which a nucleic acid construct can be directly introduced into the DNA of a DNA-containing organelle such as a chloroplast.

There are two principle methods of effecting stable genomic integration of exogenous sequences, such as those included within the nucleic acid constructs of the present invention, into plant genomes:

*Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Amtzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Regardless of the transformation technique employed, once procollagen or collagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the collagen is typically harvested. Plant tissues/cells may be harvested at any time (e.g. at maturity), and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes.

For the generation of atelocollagen or collagen, the propeptide or telopeptide-comprising collagen may be purified from the genetically engineered cells prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to salting out with ammonium sulfate or the like and/or removal of small molecules by ultrafiltration or by chromatographic methods.

According to one embodiment, the protease used for cleaving the recombinant propeptide or telopeptide comprising collagen is not derived from an animal. Exemplary proteases include, but are not limited to certain plant derived proteases e.g. ficin (EC 3.4.22.3) and certain bacterial derived proteases e.g. subtilisin (EC 3.4.21.62), neutrase. According to a particular embodiment, the protease is ficin. The present inventors also contemplate the use of recombinant enzymes such as rhTrypsin and rhPepsin. Several such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog # PW201041) and TrypZean™, a recombinant human trypsin expressed in corn (Sigma catalog #T3449).

Irrespective of how it is generated or isolated, collagen is typically solubilized in an acid solution where it is present in its monomeric form (i.e. non-fibrillated form). Exemplary acids for solubilizing monomeric collagen include, but are not limited to hydrochloric acid (HCl) and acetic acid.

As used herein, the phrase "collagen monomers" refers to monomeric collagen that has not undergone the process of fibril assembly.

The collagen may be present in the acid solution at a concentration of about 1-100 mg/ml. According to a particular embodiment, the collagen is present in the acid solution at a concentration of about 3-20 mg/ml. An exemplary concentration of HCl which may be used to solubilize collagen monomers is about 10 mM HCl.

According to one embodiment a concentration of about 0.05 mM-50 mM acetic acid is used to solubilize the collagen monomers. An exemplary concentration of acetic acid which may be used to solubilize collagen monomers is about 0.5 M acetic acid.

Following solubilization of the collagen, the collagen may optionally be treated so as to promote fibrillogenesis thereof.

The term "fibrillogenesis" as used herein refers to the precipitation of soluble collagen in the form of fibrils.

Fibrillogenesis is entropy driven—the loss of water molecules from monomer surfaces drives the collagen monomers out of solution and into assemblies with a circular cross-section, so as to minimize surface area. Fibrillogenesis may be performed in a variety of ways including neutralization of the pH, increasing the temperature and/or the ionic strength.

An exemplary alkaline solution that may be added to increase the pH of the collagen is $Na_2HPO_4$ (pH 11.2). Typically, an amount of alkaline solution is calculated such that the final pH of the collagen is about 7-7.5 (e.g. 7.4). $Na_2HPO_4$ (162 mM) is typically added at a ratio of 1:7-1:9 v/v.

According to a particular embodiment, the collagen is present in the composition at a concentration between 10-50 mg/ml, more preferably between 20-30 mg/ml.

In order to generate the composition described herein a mixture of collagen and inorganic salts may be prepared.

The inorganic salt may be a sodium salt, chloride salt, potassium salt, calcium salt, magnesium salt, phosphate salt, sulfate salt or a carboxylate salt.

Preferably, the inorganic salt is selected from the group consisting of NaCl, KCl, CsCl, $CaCl_2$, CsF, $KClO_4$ $NaNO_3$ and $CaSO_4$.

According to a particular embodiment, the inorganic salt is $CaCl_2$.

The $CaCl_2$ is added such that it is present at a final concentration between 5-100 mM, more preferably between 7-60 mM, more preferably between 10-50 mM and even more preferably between 10-30 mM.

According to a preferred embodiment, the $CaCl_2$ is added such that it is present at a final concentration of about 20 mM.

Additional components may be added to this mixture including for example the effect of additional bio-polymers and/or or ceramic particles.

The bio-polymer may include chitosan, hyaluronic acid, alginate, gelatin, silk, elastin, polylactic and/or lactic acid, the like, and combinations thereof.

Examples of particles which can be used according to the teachings of the present invention include, but are not limited to, calcium titanate, hydroxylapatite (HA), tricalcium phosphate (TCP), biphasic calcium phosphate and other calcium phosphates and calcium-phosphorus compounds, hydroxylapatite calcium salts, corraline hydroxyapatite, calcium carbonate inorganic bone, dental tooth enamel, aragonite, calcite, nacre, graphite, pyrolytic carbon, bioglass, bioceramic, and mixtures thereof.

Prior to addition of the inorganic salt, the fibrillated collagen may be crosslinked. Crosslinking of the fibers may be effected using any one of the below methods: 1. by glutaraldehyde, N-ethyl-N'[3-dimethylaminopropyl] carbodiimide (EDC) in the presence or absence of N-hydroxysuccinimide (NHS), PEG Dendrimers and Multi-arm PEGs, genipin or other chemical crosslinking agents; 2. by glycation using different sugars; 3. by Fenton reaction using metal ions such as copper; 4. by lysine oxidase; 5. by UV radiation (for example in the presence of a photoinitiator such as 4-(2-hydroxyethoxy)phenyl-(2-hydroxy-2-propyl)ketone—Irgacure 2959) or 6. by dehydrothermal (DHT) crosslinking.

The present invention contemplates that the crosslinking may be effected following the addition of the inorganic salts as well (e.g. the organic salt may be added, after which the crosslinking may be performed using DHT).

According to one embodiment, the concentration of EDC is selected to be within the range of 10-50 mM.

According to another embodiment, the number of days DHT crosslinking is effected is between 1 and 5 days.

Selection of the amount of crosslinker and/or the amount of time for which the collagen is crosslinked is selected according to the requirements of clot stability and growth factor release, as further described herein below.

Following generation of the collagen/inorganic salt mixture, the mixture may optionally be dried.

According to a particular embodiment, the collagen/salt mixture is frozen and freeze-dried.

Typically, freeze-drying is achieved through the use of standard commercial freeze-drying equipment. In a particular embodiment, the freeze-drying of the mixture facilitates the formation of a porous structure throughout.

Following the optional drying stage, the mixture is contacted with PRP. It will be appreciated that if the mixture is dried, pre-hydration with a suitable liquid is also contemplated. Such liquids include physiological buffers (e.g. PBS) and/or solutions of platelet poor plasma (PPP).

The phrase Platelet-Poor Plasma (PPP) refers to blood plasma with very low number of platelets (typically less than $10\times10^3/\mu L$).

Typically the PPP is prepared from the same whole blood sample for which the PRP is prepared.

The generated composition may be in a liquid state or a semi-solid state. For example at temperatures below about 37° C., the composition is in a liquid state. When the temperature is about 37° C., activation of the PRP occurs and a jelly-like substance (clot) is generated.

Preferably the composition is capable of producing a clot at 37° C. in about 5-10 minutes, more preferably between about 6-7 minutes in vitro.

The present inventors propose that when in a semi-solid state or a solid state the collagen fibers transform the clot into a composition that is suturable.

As mentioned, the ratio of the components in the composition and state of the components (e.g. crosslinked or non-crosslinked collagen) dictates the physical parameters of the clot.

Thus, according to another aspect, there is provided a composition of matter comprising collagen, platelet rich plasma (PRP) and an inorganic salt, being capable of releasing more than 3000 pg/ml of platelet derived growth factor (PDGF) following 10 days of incubation at 37° C. under in vitro conditions.

Methods of assaying growth factors are known in the art including for example by immunoassays, Western blot and/or Real-time PCR.

According to another embodiment, the composition is capable of releasing more than 3500 pg/ml of platelet derived growth factor (PDGF) following 10 days of incubation at 37° C. under in vitro conditions.

According to another embodiment, the composition is capable of releasing more than 4000 pg/ml of platelet derived growth factor (PDGF) following 10 days of incubation at 37° C. under in vitro conditions.

According to another embodiment, the composition is capable of releasing more than 4500 pg/ml of platelet derived growth factor (PDGF) following 10 days of incubation at 37° C. under in vitro conditions.

According to another embodiment, the composition is capable of releasing more than 5000 pg/ml of platelet derived growth factor (PDGF) following 10 days of incubation at 37° C. under in vitro conditions.

According to another aspect, there is provided a composition of matter comprising collagen, platelet rich plasma (PRP) and an inorganic salt, being resistant to degradation following 20 days of incubation at 37° C. under in vitro conditions.

According to another embodiment, the composition of matter is resistant to degradation following about 25 days of incubation at 37° C. under in vitro conditions.

According to another embodiment, the composition of matter is resistant to degradation following about 30 days of incubation at 37° C. under in vitro conditions.

According to another embodiment, the composition of matter is resistant to degradation following about 35 days of incubation at 37° C. under in vitro conditions.

According to another embodiment, the composition of matter is resistant to degradation following about 40 days of incubation at 37° C. under in vitro conditions.

The compositions disclosed herein are typically used for treating wounds and/or tissue regeneration.

Thus, according to another aspect of the present invention there is provided a method of treating a wound or inducing tissue regeneration in a subject in need thereof, comprising administering to the subject a therapeutically effective amount of the composition of matter described herein, thereby treating the wound or inducing tissue regeneration.

Subjects which may be treated using the methods described herein are typically mammalian, more preferably human.

According to a preferred embodiment, the PRP used to make the composition is autologous to the subject being treated.

Tissues which may be repaired using the composition described herein include for example cartilage, meniscus, ligament, tendon, bone, skin, bone, surgical wounds, cornea, periodontal tissues, maxillofacial tissues, temporomandibular tissues, abscesses, resected tumors and ulcers.

The PRP compositions described herein (i.e. PRP, collagen and inorganic salt) may be delivered to a patient in an emergency situation or as part of an elective procedure. To treat damaged connective tissue, the PRP composition may be delivered as part of an inpatient or outpatient procedure days, weeks, months, or years after the tissue damage occurred. Examples of connective tissue damage that may be treated using PRP include, but are not limited to, lateral epicondylitis (i.e., tennis elbow), plantar fasciitis, patellar tendonitis (i.e., Jumper's Knee), Achilles tendonitis, rotator cuff tendonitis, ankle sprains, and ligament tears (partial or full). The tissue damage may be identified using one or more medical imaging technologies such as, but not limited to, x-ray imaging, magnetic resonance imaging (MRI), and ultrasound imaging. To treat damage to the myocardium, the PRP composition may be delivered in an emergency room and/or by emergency medical service providers when an MI is identified. In other instances, the PRP composition may be delivered after an MI during reperfusion therapy.

The PRP composition may be delivered at any suitable dose. In some embodiments, the dose may be between about 1 cc and about 3 cc, between about 3 cc and about 5 cc, between about 5 cc and about 10 cc, between about 10 cc and about 20 cc, or more. The dose may be delivered according to a medical procedure (e.g., at specific points in a procedure) and/or according to a schedule.

In some examples, the PRP composition may be delivered to damaged connective tissue in or around affected joints. The PRP composition may be delivered to an individual in need thereof by injection using a syringe or catheter. The PRP composition may also be delivered via a dermal patch, a spray device or in combination with an ointment, bone graft, or drug. It may further be used as a coating on suture, stents, screws, plates, or some other implantable medical device. Finally, it may be used in conjunction with a bioresorbable drug or device.

According to one embodiment, the PRP composition is incorporated into a suture material. The PRP composition may be woven into the suture material. Alternatively, the suture material could be incubated with PRP prior to use. Incubation times may be from a few seconds up to any convenient time which may be the duration of a medical procedure. The PRP may be incubated with the suture material from a few seconds to hours before use, such as less than 1 minute, 5-10 minutes, 10 minutes to an hour, 1-3 hours, 4-12 hours, 13-24 hours, 1-3 days, or 3-31 days.

The site of delivery of the PRP composition is typically at or near the site of tissue damage. The site of tissue damage is determined by well-established methods including imaging studies and patient feedback or a combination thereof. The preferred imaging study used may be determined based on the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques. The patient may also assist in locating the site of tissue injury or damage by pointing out areas of particular pain and/or discomfort.

PRP compositions that are formulated as gels or other viscous fluids may be difficult to deliver via a needle or syringe. Thus, in variations where the use of a needle or syringe is desirable, it may be desirable to add a gelling and/or hardening agent to the PRP composition in situ. One or more needles or catheters may be configured to deliver the PRP composition and/or the agent simultaneously, or substantially simultaneously, to the affected tissue. For example, if a needle is used to deliver the PRP composition, the needle may comprise a plurality of lumens through which the PRP composition and the agent separately travel. Alternatively or additionally, separate needles may be used to deliver the components to the tissue at the same time or one after the other.

The PRP composition may be delivered minimally invasively and/or surgically. For example, the PRP composition may be delivered to the heart using a catheter inserted into the patient via the femoral vein or artery, the internal jugular vein or artery, or any other suitable vein or artery. The PRP composition may be delivered along with one or more medical devices, instruments, or agents to treat the MI and/or other cardiac conditions.

The devices for injecting or delivering the PRP compositions (catheter or otherwise) may include cooled parts or other temperature control mechanisms to keep the PRP composition at a desired temperature. Various embodiments of delivery devices may include a cooled chamber, and/or an agitator mechanism in a PRP chamber or injection chamber to prevent settling or clumping of the PRP components. For example, in some variations, the catheter or other delivery device has a cooled lumen or lumens for keeping the PRP composition cool during delivery. The delivery devices may additionally or alternatively include a mixing chamber for mixing the PRP composition prior to delivery. The PRP composition may also be stored in an agitating/vibrating chamber, or the physician may agitate the PRP composition once inside the delivery device by tilting or otherwise manipulating the device.

The PRP composition may be used alone and or in combination with other therapies including, but not limited to, stems cells (embryonic or adult) progenitor cells, somatic cells, cord blood, drugs, genetically engineered molecules, or other bioactive substances.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Preparation of rhCollagen for the Different Formulations

An appropriate volume of rhCollagen stock solution (3 mg/ml, 10 mM HCl) was freeze dried and re-suspended with 1 ml DDW to obtain the required concentration. Addition of dibasic phosphate buffer (162 mM dibasic phosphate, pH 11.2) to the re-suspended concentrated rhCollagen solution (1:7 v/v) resulted in a cloudy precipitate indicating self assembly of rhCollagen molecules into fibrils due to the neutralization of the rhCollagen solution.

Part of the highly concentrated fibrillar rhCollagen solutions were cross-linked with 1-[3-(Dimethylamino)propyl]-3-ethylcarbodiamide methiodide (EDC, Sigma) at different concentrations of (20 mM, 50 mM) for 3 hours. Samples were washed twice by centrifugation at 8000 RPM for 10 minutes, by expelling the liquid in between washes.

Calcium chloride solution at a concentration of 100 mg/ml was prepared. The addition of 7 mM, 20 mM and 60 mM concentrations was tested with the rhCollagen formulations by adding the appropriate volumes to the rhCollagen-filled tubes. Both fibrillar and cross-linked fibrillar concentrated rhCollagen solutions were freeze dried.

PRP Extraction:

Autologous Platelet Preparation system (PPKE-2) PRP kit of Estar Medical was used. 10 ml of blood was withdrawn into 10 ml vacuum tube containing a gel and citrate based anticoagulant. The blood was centrifuged for 10 minutes at 1500 RCF to precipitate the red blood cells and part of white blood cells. 4 ml of poor plasma platelets were removed prior to filtration so as to obtain plasma poor platelets (PPP). Following filtration, the remaining 1.5-2 ml of plasma contained the plasma rich platelets (PRP). The PRP was mixed gently and transferred to an empty tube. The PRP was kept on ice until use.

rhCollagen Flakes with PRP Mixing:

Two methods of hydrating collagen flakes were used:

1. Direct mixing of dry rhCollagen flakes: A syringe filled with dry rhCollagen flakes with a fixed weight was used. An additional syringe was filled with PRP. The rhCollagen flakes were re-suspended and homogenized gently with the PRP solution by using a luer lock between the two syringes. The final concentrated rhCollagen-PRP suspension was transferred to one syringe and injected into a mold.

2. Mixing dry rhCollagen with PBS/PPP (poor plasma platelets) and then with PRP: A syringe filled with a fixed weight of dry rhCollagen flakes was used. An additional syringe was filled with 0.5 ml PBS/PPP to re-suspend and homogenize the rhCollagen flakes. The mixing procedure was performed by a luer lock connection between the two syringes. The obtained suspension was transferred into one of the syringes. The empty syringe was disconnected. A third syringe containing 0.5 ml PRP was connected to the syringe filled with rhCollagen suspension and mixed gently up to 3-4 times. The final concentrated rhCollagen-PRP suspension was transferred to one of the syringes and injected into a mold.

All of the samples were incubated at 37° C. in order to form a clot. The incubation time to form a clot was dependent on the calcium chloride concentration used in the formulation.

Calcium Chloride Concentrations to Optimize Time for Clot Formation:

Different calcium chloride concentrations were used to characterize the rate of PRP activation and clot formation. Calcium chloride in the concentrations of 7 mM, 20 mM and 60 mM were tested.

Growth Factors Release Study:

Different rhCollagen suspensions were mixed with PRP as described above. 200 μl aliquots of the different PRP-rhCollagen formulation were placed in transwells-8 μm mesh, suitable for 24 well plates.

Thrombin Sample Preparation:

A thrombin solution of 1,000 IU/ml was prepared from bovine thrombin powder (Sigma). First, PRP was added into the transwells followed by the addition of the thrombin solution in a 1:10 v/v thrombin:PRP ratio. PRP that were activated by $CaCl_2$ were prepared by mixing equal volume of PRP and PBS containing 20 mM $CaCl_2$. All the rhCollagen samples containing 20 mM $CaCl_2$, together with thrombin samples were then incubated at 37° C. for 15 minutes to allow clot formation. 0.5 ml of DMEM medium (1% serum) were added to each well and additional 200 μl were added into the transwell above the formed clot.

The 24-plate was incubated in a humidified incubator (5% $CO_2$, 37° C.). At various time points (1, 3, 5, 10 days) all the release medium was collected and fresh medium was added to each well. The media samples were stored in a −80° C. freezer until all samples were collected. Concentrations of human PDGF-AB and TGF-beta were determined using the commercially available Quantikine ELISA kits (R&D Systems). No dilutions were used for the cytokine detection.

Fibroblast Proliferation Assay Study:

rhCollagen suspensions (30 mg/ml) of fibrillar and fibrillar cross-linked (20 mM EDC) were mixed with PRP as described above and the proliferation of normal human dermal fibroblasts (nHDF) was analyzed in the presence of the released growth factors from clot samples. In addition, the effect of cell proliferation from activated platelets by 20 mM $CaCl_2$ and activated platelets by thrombin were analyzed. 200 ul aliquots from each formulation were inserted into transwells (3 transwells for each formulation) and 10,000 nHDFs were seeded at the bottom of each and the wells were filled with 0.5 ml DMEM+1% fetal bovine serum (FBS). The positive and negative controls for the experiment were obtained by following the same number of cells proliferating in the environment of 20% FBS and 1% FBS, respectively. The proliferation was following 3 and 7 days following seeding.

Preparation for SEM Analysis:

RhCollagen-PRP and thrombin-PRP based clot samples were prepared as described above. The samples were immediately immersed in sodium cacodylate-buffered formaldehyde-glutaraldehyde fixative for 24 hours at room temperature. The samples were washed 3 times with 0.1M cacodylate-buffer. Post fixation, the samples were stained with 1% Osmium tetroxide for 1 hour. The samples were washed again, twice with 0.1M cacodylate-buffer and twice with DDW. Subsequently, the samples were dehydrated by serial transfer in increasing concentrations of ethanol (10-100%) and infiltrated with liquid carbon dioxide before critical drying point. Finally, the samples were mounted on aluminum and coated with gold sputtering to a thickness of 250 Å.

Mechanical Characterization:

Three types of samples were prepared:

(i) rhCollagen-PRP in the presence of 20 mM calcium chloride;

(ii) thrombin-PRP; and (iii) PRP and 20 mM calcium chloride.

The samples were prepared as described above and injected into cylinder molds that fit a parallel plate geometry rheometer instrument (HAAKE, Rheostress 600). The samples were incubated at 37° C. for clot formation. Each clot sample was placed in the rheometer and a shear stress of 1-100 Pa was applied. The shear strain as a function of shear stress was recorded. The slopes of the program-processed curves for each sample were compared to estimate the sample's resistance to shear deformation and therefore its mechanical stability.

Degradation Assay:

rhCollagen and thrombin based clots were prepared as described above. 0.5 ml of each formulation was injected into 24-well plates. Duplicates from each sample were tested. Following clot formation at 37° C., 0.5 ml DMEM medium (1% serum) was added to each well. The samples size and changes in morphology were followed and assessed for up to 30 days.

Example 1

Mixing PRP with rhCollagen

Two PRP with rhCollagen mixing methods were tested. In both methods the coupling of two syringes with a luer lock was used (FIG. 1). One method was based on a direct mixing of dry rhCollagen with PRP solution (two syringes). The other method was based on two steps. First, initial hydration of rhCollagen by using PBS to form a uniform suspension followed by the mixing of the syringe filled with rhCollagen suspension with PRP solution. The clots obtained by both methods had similar physical properties as detailed below.

Example 2

The Structure of rhCollagen-Based Clot

Figure 2C:
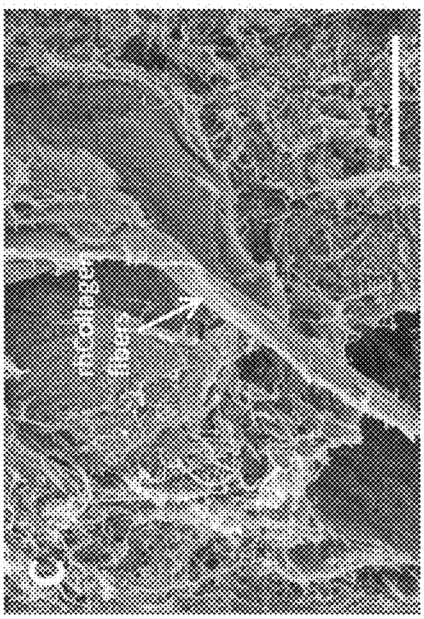
Figure 2D:
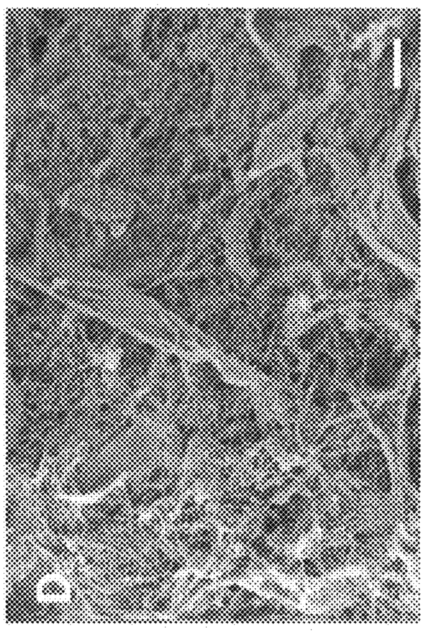

The structure of rhCollagen based clot was analyzed by using the SEM and was compared to the thrombin-based clot. The study yielded clear images of the elements that constituted the PRP gel clot when it was mixed with thrombin or when mixed with the rhCollagen. The thrombin-based PRP clot was composed of randomly arranged fibrillar elements with homogenous thickness throughout their length with platelet cell elements in a breadcrumb-like appearance arranged among them (FIGS. 2A-B). The fibrillar elements were identified as fibrin fibers. In the rhCollagen-based gel clot, in addition to the existence of fibrin together with activated platelets, islands of rhCollagen thick fibers were identified. These rhCollagen fibers were found to be entrapped within the fine mesh that was formed by the fibrin fibers (FIGS. 2C-D).

Example 3

Growth Factors Release from rhCollagen-Based Clot

The amount of PDGF-AB released from different rhCollagen-activated PRP preparations was compared with the amount of PDGF-AB released from thrombin activated PRP, calcium chloride activated PRP and self-activated PRP. As seen in FIGS. 3A-B, the release profile of PDGF over 10 days varies among the formulations. Samples that contained cross-linked (20 mM EDC) fibrillar rhCollagen at a concentration of 30 mg/ml had the highest accumulative release of PDGF relative to the variety of controls (self-activated platelets, activated platelets by using calcium chloride or thrombin). The fact that platelets that are activated by calcium chloride with no addition of collagen showed much lower PDGF release than the collagen formulation with the same calcium chloride concentration, demonstrates the active role collagen plays in the release profile of the PDGF, specifically for the cross-linked formulation. The release profile of lower concentrations of rhCollagen (10 mg/ml, 20 mg/ml) was characterized. It was found that the amount of PDGF-AB released from PRP clots activated by lower concentrations of rhCollagen were similar to the values obtained with calcium chloride activated PRP clots. Accordingly, the optimal working concentration of rhCollagen was about 30 mg/ml.

The results described above demonstrate the ability to control the PDGF release as a function of rhCollagen concentrations and in different physical states (fibrillar/fibrillar cross-linked) following mixture with PRP.

Example 4

Fibroblast Proliferation Assay Study

Quantitative measurement of cell proliferation by using WST (water soluble tetrazolume salt) demonstrates that there was a significant difference between fibroblast cell proliferation of collagen-PRP based clots and fibroblast cell proliferation of thrombin-based clots and control cells proliferating in medium with 1% fetal bovine serum (starvation condition) (FIGS. 6A-B). Significant difference among the collagen-based clots and controls (thrombin and 1% FBS) was found to increase following 7 days. Cells that surrounded the cross-linked collagen based clot had highest proliferation, even higher than cells that proliferated in the presence of medium that contained 20% FBS. In addition, the microscopy images demonstrated the high amount of cells that proliferated following 3 and 7 days surrounding fibrillated collagen based clots as compared to $CaCl_2$-PRP based clots.

Example 5

Mechanical Strength of rhCollagen Based Clot

The mechanical strength of rhCollagen based clots was characterized and compared to activated PRP by thrombin and activated PRP with $CaCl_2$. The results are depicted in FIG. 4. The deformation of clot samples and the resistance to load were measured as a function of the applied loads. A maximal shear load of up to 10P was applied on thrombin and $CaCl_2$-PRP based clots. The deformation of thrombin-based clot was high and increased to more than 400% with the applied shear load. The maximal deformation of a clot was found to be by mixing PRP together with $CaCl_2$ and PBS. This showed an increase of up to 180% in its deformation when a maximal shear load of 10 Pa was applied. In contrast, when a shear load of 10 Pa was applied on rhCollagen based clots, no deformation was detected. When a higher shear stress of up to 100 Pa was applied on both types of rhCollagen-based clots, prepared by direct mixing or first hydrated by PBS and then mixed with PBS, a deformation of 17-27% was detected. Such low deformation values were detected for all types of rhCollagen based clots that were tested, including collagen in the form of fibrillar, cross-linked and combination of both. These results emphasize the stability of rhCollagen based clots with respect to thrombin and may hint at the ability of the clot to serve as a scaffold for longer periods of time and therefore release growth factors in a sustained and gradual fashion.

Example 6

In-Vitro Degradation Assay of rhCollagen Based Clot

The degradation of different rhCollagen based clots was compared with thrombin-based clot and by the activation of platelets by $CaCl_2$ alone. Changes in clot size and morphology were tracked for 30 days. The degradation of thrombin based clot (FIGS. 5A-B, blue circles) started at day 7 and was completely dissolved by day 12. On the other hand, different rhCollagen flakes configurations (fibrillar, fibrillar and cross-linked) were mixed directly with PRP or mixed first with PBS and then with PRP to form clots and found to be stable and did not degrade following 30 days of incubation. The above described results strengthen the notion that rhCollagen based clots are considerably more stable than thrombin-based clots and therefore may remain in the tissue for longer periods of time to allow a sustained release of growth factors and therefore increase healing efficacy.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing a composition of matter for treating a wound or inducing regeneration of tissue comprising:

(a) contacting solubilized recombinant collagen with $Na_2HPO_4$, so as to generate fibrillated collagen, wherein said $Na_2HPO_4$ is present at a concentration between 16.2 mM and 20.25 mM;

(b) crosslinking said fibrillated collagen using N-ethyl-N'-[3-dimethylaminopropyl] carbodiimide (EDC) to generate crosslinked, fibrillated collagen;

(c) generating a mixture of said crosslinked, fibrillated collagen and inorganic salt; and (d) contacting said mixture with platelet rich plasma (PRP), thereby producing the composition of matter for treating a wound or inducing regeneration of tissue.

2. The method of claim 1, wherein said inorganic salt is selected from the group consisting of sodium salt, chloride salt, potassium salt, calcium salt, magnesium salt, phosphate salt, sulfate salt and a carboxylate salt.

3. The method of claim 1, further comprising drying said mixture prior to said contacting of step (d).

4. The method of claim 3, wherein said drying comprises freeze-drying.

5. The method of claim 3, further comprising hydrating said mixture following said drying with a hydrating solution prior to said contacting.

6. The method of claim 5, wherein said hydrating solution comprises platelet poor plasma (PPP).

* * * * *